United States Patent
Tsubouchi et al.

(10) Patent No.: US 7,901,668 B2
(45) Date of Patent: Mar. 8, 2011

(54) SILK FIBROIN EMULSIFIER AND PROCESS FOR THE PRODUCTION THEREOF

(75) Inventors: Kozo Tsubouchi, Tsukuba-gun (JP); Shoko Fujiura, Osaka (JP)

(73) Assignees: Eaudelman Co., Ltd., Osaka-shi (JP); National Institute of Agrobiological Sciences, Tsukuba-shi (JP)

( * ) Notice: Subject to any disclaimer, the term of this patent is extended or adjusted under 35 U.S.C. 154(b) by 1039 days.

(21) Appl. No.: 10/497,113

(22) PCT Filed: Dec. 26, 2001

(86) PCT No.: PCT/JP01/11450
§ 371 (c)(1),
(2), (4) Date: May 27, 2004

(87) PCT Pub. No.: WO03/045336
PCT Pub. Date: Jun. 5, 2003

(65) Prior Publication Data
US 2004/0265260 A1    Dec. 30, 2004

(30) Foreign Application Priority Data
Nov. 29, 2001 (JP) ................ 2001-364489

(51) Int. Cl.
*A61K 8/64* (2006.01)
*A61K 8/06* (2006.01)

(52) U.S. Cl. ........................ 424/70.14; 424/401

(58) Field of Classification Search ............ 424/401
See application file for complete search history.

(56) References Cited

U.S. PATENT DOCUMENTS

| | | | |
|---|---|---|---|
| 4,826,818 A | 5/1989 | Mori et al. | |
| 5,951,506 A | 9/1999 | Tsubouchi | |
| 6,066,352 A | 5/2000 | Ogasawara et al. | |
| 6,175,053 B1 | 1/2001 | Tsubouchi | |
| 6,218,357 B1 | 4/2001 | Terauchi | |
| 6,440,740 B1 | 8/2002 | Tsubouchi et al. | |
| 2003/0165548 A1 | 9/2003 | Tsubouchi et al. | |

FOREIGN PATENT DOCUMENTS

| | | |
|---|---|---|
| EP | 0 823 258 | 2/1998 |
| JP | 58 105907 | 6/1983 |
| JP | 60-112800 | 6/1985 |
| JP | 63-283735 | 11/1988 |
| JP | 01-233300 | 9/1989 |
| JP | 05-025024 | 2/1993 |
| JP | 05-056751 | 3/1993 |
| JP | 05-070332 | 3/1993 |
| JP | 05-078232 | 3/1993 |
| JP | 06-157234 | 6/1994 |
| JP | 06-279254 | 10/1994 |
| JP | 08-020792 | 1/1996 |
| JP | 08-268905 | 10/1996 |
| JP | 08-295697 | 11/1996 |
| JP | 09-023837 | 1/1997 |
| JP | EP 0920875 A1 * | 6/1999 |
| JP | 11-276876 | 10/1999 |
| JP | 2000-073090 | 3/2000 |
| WO | WO 01/42300 | 6/2001 |

OTHER PUBLICATIONS

Ni, Li et al., "Functional Properties of Silk Fibroin", Wuxi Qinggong Daxue Xuebao (2001), 20(2), pp. 128-132, (1 page English abstract).

* cited by examiner

*Primary Examiner* — Sreeni Padmanabhan
*Assistant Examiner* — Sahar Javanmard
(74) *Attorney, Agent, or Firm* — Flynn, Thiel, Boutell & Tanis, P.C.

(57) ABSTRACT

To provide an emulsifier for cosmetic use which not only has an improved emulsifying power and feel during use, but wherein the emulsifier itself has a skin cell growth-promoting property. The emulsifier contains an aqueous solution of silk protein composed mainly of amorphous silk fibroin, wherein the aqueous solution of silk protein composed mainly of amorphous silk fibroin is an aqueous solution of silk protein obtained by dissolving unscoured, partially scoured or scoured spun silkworm fibers (cocoon filaments) with a neutral salt and then dialyzing the solution.

6 Claims, 4 Drawing Sheets

SILK FIBROIN EMULSIFIER AND PROCESS FOR THE PRODUCTION THEREOF

TECHNICAL FIELD

1. Technical Field to which the Invention Relates

The present invention relates to a protein-based emulsifier and to a method of producing emulsified cosmetic materials using the emulsifier.

2. Prior Art

Anionic, cationic, amphoteric and nonionic surfactants have conventionally been used as emulsifiers for production of emulsified cosmetic materials by emulsification of water and oily substances.

However, since synthetic surfactants have been implicated in the destruction of skin surface tissue and constituting a cause of liver damage when entering the body, research and development have been directed toward devising emulsifiers using safer naturally-derived raw materials.

In particular, numerous naturally-derived protein-based emulsifiers have been proposed because of their high safety and generally excellent affinity for skin surface tissue.

Because most protein-based emulsifiers have inferior emulsifying power compared to synthetic surfactants, research on them has tended to be focused on increasing their emulsifying power by chemical modification (chemical transformation treatment), and development examples of such include the following.

Emulsifiers comprising amino acid alkyl esterified proteins containing alkyl groups with carbon chain lengths of 14-24 (Japanese Unexamined Patent Publication No. Sho-60-112800).

Protein-based emulsifiers comprising amide-bonded amino group-containing amino acid esters at the carboxyl termini of hydrophilic protein decomposition products (Japanese Unexamined Patent Publication No. Sho-60-175531).

Emulsifiers comprising lecithin-gluten complexes or lecithin-globin complexes (Japanese Unexamined Patent Publication No. Sho-63-283735).

Emulsifiers composed mainly of functional proteins comprising activated branched polysaccharides and proteins bonded together (Japanese Unexamined Patent Publication No. Hei-1-233300).

Emulsifiers comprising complexes of proteins or their hydrolysis products with phospholipids (Japanese Unexamined Patent Publication No. Hei-5-70332).

Emulsifiers comprising protein complexes with lysophospholipids, free fatty acids and proteins bonded together (Japanese Unexamined Patent Publication No. Hei-5-56751).

A method of using as the emulsifier a surfactant phase obtained by mixing a hydrolysate produced using a protease to treat elastin present in the nuchal ligament of an animal such as a cow, or an aqueous solution of the hydrolysate, with a polyhydric alcohol (Japanese Unexamined Patent Publication No. Hei-6-279254).

Emulsifiers containing at least 40% of an IIS globulin basic subunit in pulse protein (Japanese Unexamined Patent Publication No. Hei-9-23837).

Emulsifiers comprising bonded combinations of proteins with saponins or bile acids (Japanese Unexamined Patent Publication No. Hei-11-215956).

The raw material proteins used for these development examples are primarily, for example, plant proteins such as soybean protein and wheat protein, and animal proteins such as collagen, gelatin, elastin, egg albumin, serum albumin, egg yolk lecithin, milk casein, myosin and fibrinogen.

Incidentally, because silk protein is a substance with excellent bioadaptability, it is receiving attention for use in cosmetic products, and cosmetic materials containing various silk proteins have been proposed.

As development examples there may be mentioned a detergent with improved feel during use obtained by adding a water-soluble silk peptide (silk fibroin-derived) comprising 2-50 amino acid units (average molecular weight: 200-5,000) to an amidocarboxylic acid-type surfactant (Japanese Unexamined Patent Publication No. Hei-8-20792), a liquid cosmetic material obtained by adding a fibroin hydrolysate as a humectant (Japanese Unexamined Patent Publication No. Hei-6-157234), a bath additive which gives an enhanced feeling after bathing by containing an added water-soluble silk fibroin hydrolysate (Japanese Unexamined Patent Publication No. Hei-5-78232), a shampoo containing a water-soluble silk fibroin hydrolysate with a molecular weight of about 1,000 in addition to vitelline oil, as a conditioning agent (Japanese Unexamined Patent Publication No. Hei-5-25024), and a gelled creamy humectant comprising a dispersing medium in which there is dispersed a microstructure obtained by adding carbon dioxide to an aqueous fibroin solution and then adjusting the pH of the aqueous fibroin solution to near the isoelectric point by addition of an acid (Japanese Unexamined Patent Publication No. Hei-10-251299) (where the purpose is to adjust the pH of the aqueous fibroin solution to near the isoelectric point with an acid to gel it, but the aqueous fibroin solution is not used as an emulsifier.)

However, none of these examples use silk protein as an emulsifier for cosmetic materials.

Very recently there have been proposed inventions employing silk proteins as surfactants (Japanese Unexamined Patent Publication No. Hei-11-276876, Japanese Unexamined Patent Publication No. 2000-73090).

These inventions are for surfactants containing cocoon- or raw silk-extracted sericin or sericin decomposition products as the effective components, and they are considered useful in a very wide range of fields including pharmaceuticals, quasi drugs, cosmetics, foods, household detergents and the like.

Incidentally, although emulsified cosmetic materials obtained using protein-based emulsifiers generally have a soft, moist feel during use, it is often the case that when handled during actual use, they produce a crumbling feel and lack spreadability.

The important factors for emulsifiers used in cosmetic products include not only safety and emulsifying power but also feel during use, and therefore all of these aspects must be carefully considered when designing emulsified cosmetic formulations.

Meanwhile, in the course of many years of research on silk, the present inventors have found that silk fibroin has an effect of promoting the growth of human cells, and have proposed its use for wound covering materials and the like (Japanese Unexamined Patent Publication No. Hei-9-192210, Japanese Unexamined Patent Publication No. Hei-11-253155).

The effect was demonstrated to derive from the fibroin H chain and L chain of silk fibroin (Japanese Unexamined Patent Publication No. 2001-163899, Japanese Patent Application No. 2001-180169).

However, despite the cell growth-promoting effect of silk protein, the use of its aqueous solutions or gels as emulsifiers has not been known.

This is believed to be primarily because of the tendency of fibroin aqueous solutions and gels to fibrillate under the strong shear force of stirring and the like, and the resultant separation of the fibers (water-insoluble aggregates).

Problems to be Solved by the Invention

Most conventional protein-based emulsifiers are obtained by chemical treatment (chemical modification) of raw protein materials to improve their emulsifying power for practical use, and some few positive results have been achieved.

However, when raw protein materials are altered by chemical modification, several reaction steps must be accomplished in order to obtain the target protein-based emulsifier, and a particular problem has been the extreme difficulty of removing the unreacted reagents, which can affect the skin, from the reaction system in order to obtain pure emulsifiers containing no impurities.

It is an object of the present invention to solve the aforementioned problems by providing an emulsifier for cosmetic use which not only has improved emulsifying power and feel during use, but wherein the emulsifier itself has a skin cell growth-promoting property.

DISCLOSURE OF INVENTION

Means for Solving the Problems

The present invention, which has been accomplished under these circumstances, is the result of the discovery that a silk protein aqueous solution that can be obtained without special chemical modification exhibits excellent properties as an emulsifier for cosmetic materials and the like.

In other words, the invention provides (1) an emulsifier comprising an aqueous solution of silk protein composed mainly of amorphous silk fibroin.

The invention further provides (2) an emulsifier for cosmetic use comprising an aqueous solution of silk protein composed mainly of amorphous silk fibroin.

The invention still further provides (3) a method for production of an emulsified cosmetic material, whereby an emulsifier comprising an aqueous solution of silk protein composed mainly of amorphous silk fibroin is used for emulsification of an oily component.

The invention still further provides (4) an emulsified cosmetic material obtained by using an emulsifier comprising an aqueous solution of silk protein composed mainly of amorphous silk fibroin for emulsification of an oily component.

The invention still further provides (5) an emulsifier comprising an aqueous gel of silk protein composed mainly of amorphous silk fibroin.

The invention still further provides (6) an emulsifier for cosmetic use comprising an aqueous gel of silk protein composed mainly of amorphous silk fibroin.

The invention still further provides (7) a method for production of an emulsified cosmetic material, whereby an aqueous gel of silk protein composed mainly of amorphous silk fibroin is used for emulsification of an oily component.

The invention still further provides (8) an emulsified cosmetic material obtained by using an aqueous gel of silk protein composed mainly of amorphous silk fibroin for emulsification of an oily component.

The invention still further provides (9) the aforementioned emulsifier for cosmetic use wherein the aqueous solution of silk protein composed mainly of amorphous silk fibroin is an aqueous solution of silk protein obtained by dissolving unscoured, partially scoured or scoured spun silkworm fibers (cocoon filaments) with a neutral salt and then dialyzing the solution.

The invention still further provides (10) an emulsifier for cosmetic use wherein the aqueous gel of silk protein composed mainly of amorphous silk fibroin is an aqueous gel of silk protein obtained by gelling a silk protein aqueous solution obtained by dissolving unscoured, partially scoured or scoured spun silkworm fibers (cocoon filaments) with a neutral salt and then dialyzing the solution.

Effects of the Invention

The aqueous solution or aqueous gel of silk protein composed mainly of amorphous silk fibroin according to the invention not only exhibits enhanced emulsifying power and feel during use, but the emulsifier itself also has an effect of promoting skin cell growth.

Emulsions obtained by emulsifying oily components using this emulsifier can be used in emulsified cosmetic materials having a wide range of oil/water compositions, while also being highly superior in terms of skin care.

BEST MODE FOR CARRYING OUT THE INVENTION

Embodiment of the Invention

The aqueous solution of silk protein composed mainly of amorphous silk fibroin or the aqueous gel of silk protein composed mainly of amorphous silk fibroin according to the invention may be mixed with an oily component to achieve uniform emulsification between the water in the aqueous solution or aqueous gel of the silk protein and the oily component. In addition, since silk fibroin has an effect of promoting skin cell growth, it is possible to obtain an emulsifier for cosmetic use having an improved emulsifying powder and feel during use, while the emulsifier itself also exhibits a property of promoting skin cell growth.

The present invention encompasses the mode whereby 1) unscoured, partially scoured or scoured spun silkworm cocoon filaments or raw silk, silk yarn, silk knitted fabrics and the like as processed cocoon filaments are used as the raw material, 2) the raw material is dissolved with a neutral salt and then dialyzed with water, 3) The obtained silk protein aqueous solution is (a) utilized directly as an emulsifier or (b) the silk protein aqueous solution is first dried to obtain the dry amorphous silk substance, which for use as an emulsifier is dissolved in water to regenerate the silk protein aqueous solution for use as an emulsifier, or 4) the silk protein aqueous solution is allowed to stand in an atmosphere at 40-130° C. and preferably 50-80° C. for gelling, and the aqueous gel is used as an emulsifier.

The emulsifier prepared in this manner may then be subjected to a mixing and stirring step with the addition of the cosmetic oily component and if necessary various cosmetic additives, in order to obtain the desired latex-type or cream-type emulsion for cosmetic use.

As emulsified cosmetic materials or quasi drugs to be produced using the emulsifier of the invention there may be mentioned, for example, cleansing cosmetic products (cosmetic soaps, facial cleansers, shampoos, rinses, etc.), hair cosmetic products (hair dyes, hair cosmetics, etc.), basic cosmetic products (general creams, latexes, shaving creams, cosmetic water, eau de cologne, shaving lotions, cosmetic oils, packs, etc.), makeup cosmetic products (foundations, eyebrow paints, eye creams, eye shadows, mascaras, etc.), aromatic cosmetic products (perfumes, etc.), sunburn/sunscreen cosmetic products (sunburn/sunscreen creams, sunburn/sunscreen lotions, sunburn/sunscreen oils, etc.), nail cosmetic products (nail creams, etc.), eye liner cosmetic products (eye liners, etc.), lip cosmetic products (lipsticks, lip creams, etc.), oral cosmetic products (toothpastes, etc.), bath cosmetic products (bath cosmetics, etc.), and the like.

The method of carrying out the present invention will now be explained in detail.

A. Raw Material

The raw material substance of the silk protein as the main component of the amorphous silk fibroin of the invention may be any protein fiber substance spun by silk thread producing insects, including both domesticated silkworms and wild silkworms, such as cocoon filaments, raw silk, silk knitted fabrics or silk yarn (fibroin fibers), either with the stringy residue or in unscoured, partially scoured or scoured form, or else fibers, powders, films or the like prepared using the above as the raw material.

Silkworms generally secrete silk in the silk gland cavity of the body, and this silk is referred to as liquid silk.

Liquid silk is composed of fibroin and sericin (known as "silk proteins"), and liquid fibroin has a molecular weight of about 370,000 (Tashiro Yutaka and Otsuki Eiichi, Journal of Cell Biology, Vol. 46, p. 1 (1970)).

The fibroin with a molecular weight of about 370,000 is composed of a molecular weight of about 350,000 (H chain) and about 25,000 (L chain).

The silkworm spins the liquid silk during cocooning to form a cocoon (made of cocoon filaments and pupa).

It is known that fibroin is present at the center of the cocoon filaments while sericin is present around the perimeter, in a ratio of (70-80%) fibroin:(20-30%) sericin. The raw silk is made by assembling together from several to several dozen cocoon filaments.

Fabrics woven from raw silk are called raw silk fabrics.

Scouring is the process by which sericin is removed from cocoon filaments, raw silk or raw silk fabrics, and the scoured fibers are silk yarn or fibroin fibers.

Silk yarn is prepared by first drying the cocoon produced by sericulturing, cooking it and then reeling it to prepare raw silk, and finally scouring the raw silk or raw silk fabric to make silk-yarn or a silk knitted fabric.

The waste produced by this procedure consists of stringy residue.

The cocoon drying is accomplished by gradually reducing the temperature from 115-120° C. to a temperature of about 80° C. over a period of 5-6 hours. For the silk cooking, it is treated for 10 minutes with water vapor or hot water at 100-105° C.

B. Scouring

The scouring method is most commonly boiling in an aqueous solution containing an alkali sodium salt or soap (alkali/soap scouring).

The scouring may be carried out with only an alkali sodium salt (alkali scouring), by immersion in pressurized hot water (for example, 120° C. hot water) or by scouring with an enzyme (enzyme scouring).

Boiling scouring may also be accomplished with water alone, but it is not common because it leaves residue of sericin.

Silk yarn is obtained by the scouring.

When scouring is not carried out, the threads are described as unscoured, and when the scouring is incomplete, they are described as partially scoured.

The stringy residue obtained by partial scouring is also referred to as silk yarn, but is not referred to as fibroin fibers.

The term fibroin fibers is applied only when fibroin constitutes at least 99% of the composition.

The alkali aqueous solution used for scouring of the raw material may be an aqueous solution of an alkali sodium salt such as sodium carbonate, sodium hydrogen carbonate, sodium silicate, sodium metasilicate, sodium phosphate, sodium hydroxide or the like.

In the case of alkali scouring, a sodium carbonate aqueous solution is particularly preferred because it gives a suitable buffering effect.

The scouring removes sericin from the raw material.

Silk protein may be obtained as the emulsifier of the invention not only by preparing silk yarn by scouring, but also without scouring of the raw material or partial scouring whereby the scouring is interrupted during the process.

(Sericin) cocoon filaments made by sericin silkworms, which are mutants of domesticated silkworms, may be added during preparation of an aqueous solution composed mainly of amorphous fibroin.

Sericin is a protein having structural units composed primarily of serine (3-hydroxyalanine), and consisting of mainly segments with hydrophilic methylol groups on the side chains; it is considered to exhibit a stronger function as a humectant compared to fibroin which contains numerous non-hydrophilic groups on the side chains.

Specifically, fibroin is composed of the repeating unit -Gly-Ser-Gly-Ala-Gly-Ala-, and since the composition of non-hydrophilic groups is the 5-member unit -Gly-Ala-Gly-Ala-Gly- for each hydrophilic -Ser- unit the hydrophilic-lipophilic balance (HLB) is in a medium range, allowing the preparation of a wide range of emulsions from O/W type emulsions to W/O type emulsions, while sericin, which is formed mainly of constituent units with hydrophilic groups, is thought to have a superior humidifying function rather than emulsifying power, as compared to fibroin.

Incidentally, sericin has been reported to consistently exhibit 15% greater hygroscopicity than fibroin (Kataoka, Kozo, "Liquid silk and cocoon filament content with domesticated silkworm spinning", Journal of the Japanese Society of Sericultural Science, Vol. 50, No. 6, pp. 478-483 (1981)).

When some sericin is present, fibrillation by shear is prevented and the humectant property is increased, often providing an effective function as a skin care material.

C. Preparation of Silk Protein Aqueous Solution

Since silk is subjected to a high-temperature, high-humidity treatment with alkali agents in processing steps such as scouring, the silk protein tends to decompose to a lower molecular weight.

Silk protein is readily decomposed to a lower molecular weight by acid and alkali treatments, high temperatures (particularly at high humidity) and light (particularly ultraviolet light and radiation).

The molecular weight also tends to be reduced upon dissolution with a neutral salt.

Since the molecular weight reduction of silk protein is associated with lower cell growth promotion by the silk protein, drastic molecular weight reduction is not preferred.

Silk protein for use as an emulsifier according to the invention is obtained by dissolving the aforementioned raw materials in the following manner.

The neutral salt used as the silk dissolving agent may be a neutral salt such as, for example, calcium chloride, copper ethylenediamine, sodium thiocyanate, lithium thiocyanate, lithium bromide, magnesium nitrate or the like.

The neutral salt is preferably in a concentration of a saturated aqueous solution or at least 50% saturation (weight (g)/volume (mL)).

For the step of dissolving the silk in the neutral salt solution, an alcohol such as methyl alcohol, ethyl alcohol or propyl alcohol may be added to the neutral salt and dissolution carried out at a temperature of no higher than 94° C., and preferably a temperature of about 75-85° C.

Stirring at this time will accelerate the dissolution.

Dissolution will be hampered by a lower dissolution temperature.

Although a higher dissolution temperature will facilitate the dissolution, it will also result in more drastic molecular weight reduction.

The solution of the silk in the neutral salt contains fibroin or a mixture of fibroin and sericin, the neutral salt, the alcohol, etc.

The insolubles are first removed from the solution, and then a dialysis membrane or dialysis apparatus is used to remove the low molecular weight substances of about 5,000 and lower.

The dialysis yields a silk protein aqueous solution.

The silk protein aqueous solution may contain a calcium chloride residue of about 0.001-0.1 M.

The silk protein in the aqueous solution tends to fibrillate more readily by shear of vibration or stirring if it has a higher molecular weight.

The fibrillated protein consists of water-insoluble masses which are a cause of a reduced pleasant feel (touch) during use for cosmetic materials.

It is therefore preferred for the molecular weight of the silk protein to be reduced to some extent, although high molecular weight silk protein may also be included since it helps prevent fibrillation by allowing gentler methods of emulsification and use.

Fibroin with a (weight) average molecular weight of 5,000 or greater acts as an emulsifier.

However, almost no cell growth effect is exhibited with an average molecular weight of 5,000-20,000.

With an average molecular weight of 20,000-40,000, the cell growth effect is lower, but the fibroin may be used as an emulsifier according to the invention.

The fibroin average molecular weight sufficient for cell growth promotion is between 40,000 and 370,000.

Consequently, the most preferred range for the average molecular weight is from 60,000 to 300,000 for use as a skin care material.

D. Preparation of an amorphous powder or film from an aqueous solution of silk protein composed mainly of amorphous silk fibroin, and redissolution thereof in water for repreparation of silk protein aqueous solution The aqueous solution of C. above may be cast onto a smooth solid surface and dried to produce an amorphous silk film which is then reimmersed in water to obtain a silk aqueous solution.

The amorphous silk protein may be in the form of a powder instead of a film.

In the case of a powder, the silk protein aqueous solution may be obtained by spray drying, lyophilization and the like.

According to the invention, amorphous silk fibroin is fibroin with a crystallization degree of less than 10% (see Japanese Unexamined Patent Publication No. Hei-11-70160).

The crystallization degree of less than 10% also applies when silk sericin is included.

When the crystallization degree is less than 10%, the solution is very soft and similar to an aqueous gel even if a portion of the silk protein dissolves and a portion absorbs water and floats when the silk protein is immersed in the water, thus exhibiting action as an emulsifier.

In this case, further drying and redissolution steps are required, rendering it disadvantageous in terms of the number of steps as compared to using the silk protein aqueous solution directly as an emulsifier.

However, amorphous silk has the advantages of being able to be stored for long periods of several years indoors in the absence of light and at a relative humidity of about 50% or lower, and of being lightweight for efficient long-distance transport since it is dry.

The silk protein aqueous solution may also be obtained from liquid silk.

For example, the silk protein aqueous solution may be obtained by removing the gel-like contents (liquid silk) from the middle or posterior silk gland of the silkworm and dissolving them in water.

However, this method requires dissection of the silkworm, removal of the silk gland from the silkworm body and further removal of the liquid silk from the silk gland cavity.

The amount of silk obtained from one silkworm is at most about 0.4 g, and since impurities tend to be included in the silkworm body fluid or silk gland cells and effort is required to obtain the silk, this process is not suitable for industrial production.

The material used according to the invention may be the industrially advantageous cocoon shell or cocoon filaments from raw cocoons, dry cocoons or boiled cocoons, or else raw silk, knitted silk or the stringy residue thereof.

E. Emulsification of the oily component by the silk protein aqueous solution

The oily component may be a vegetable oil such as olive oil, camellia oil, avocado oil, cacao oil, sunflower oil, persic oil, palm oil, castor oil or the like, or an animal oil, or even jojoba oil, a wax such as beeswax, or any of the oils or waxes listed in the Cosmetic Raw Material Standards.

The type of oily component does not significantly affect the properties of the emulsion.

The proportion of the oily component with respect to the silk protein aqueous solution concentration and the silk protein aqueous solution volume may be appropriately adjusted to prepare the desired cosmetic material.

The method of mixing the silk protein aqueous solution and oily component for emulsification may be stirring, grinding or the like.

The machine used for emulsification is preferably selected depending on the silk concentration and the oil proportion.

The viscosity of the emulsion will differ depending on the concentration of the silk aqueous solution, with a weaker silk aqueous solution concentration resulting in a lower cell growth rate by the silk protein.

The concentration is therefore at least 0.1%, and preferably at least 0.5%.

On the other hand, a higher silk protein aqueous solution concentration reduces its spreadability on the skin, resulting in a poor feel during use.

The concentration is therefore no greater than 15%, and preferably no greater than 10%.

The sericin proportion preferably does not exceed 50% because the sericin properties become dominant and gelling occurs more easily.

The upper limit is more preferably 30%.

When the silk protein aqueous solution concentration of the emulsion is low (about 3% or lower) it becomes liquid, and may be used as latex.

As the concentration increases (above about 3%), it becomes viscous and may be used as creams or ointments.

The lower cell growth rate with lower silk fibroin concentration and the reduced spreadability with higher silk protein aqueous solution concentration also apply in the case of the aqueous gel emulsion described below.

F. Gelling of Silk Protein Aqueous Solution

Gelling is achieved by allowing the silk protein aqueous solution to stand for a period. The gelling occurs faster with a higher silk protein aqueous solution concentration.

With a concentration of 3%, a period of about one week is required for gelling at room temperature (25° C.±5° C.), and the gelling time rapidly lengthens as the temperature falls below room temperature.

When the silk fibroin aqueous solution is allowed to stand at above room temperature, and particularly at 40° C. or above, gelling occurs within about 2 days. Use of an autoclave (120° C.) allows gelling to occur in about 1-2 hours.

The gelling is preferably accomplished by stationing at a temperature of 50-80° C.

It is conjectured that when the fibroin concentration of the silk protein aqueous gel increases above a certain level, the —C=O— and —NH— groups in the fibroin chains form hydrogen bonds with other neighboring fibroin molecules, becoming loosely entangled to create a three-dimensional network.

The aqueous gel is extremely fragile and the gelled state is easily ruptured by an outside force.

Upon stirring an aqueous gel of a silk protein aqueous solution with fibroin as the main component at a content of 4.5% without adding an oily component and separating the stirred product with a centrifugal separator (8,000 rpm, 10 minutes), the silk protein concentration of the supernatant was 0.1-2.0%.

Upon adding water in the amount of the supernatant to the precipitate from which the supernatant was removed and again stirring (30 seconds) and performing centrifugal separation (8,000 rpm, 10 minutes), the silk protein aqueous solution concentration of the supernatant was also 0.1-2.0%.

A portion of this gel was stirred and exhibited a property of easily dissolving in water, and will therefore be referred to as an aqueous gel.

The silk protein aqueous solution or its aqueous gel obtained in this manner acts as an emulsifier when mixed with an oily component.

A silk protein aqueous gel which may be used as an emulsifier can also be obtained by, for example, the isoelectric point method, instead of this method according to the invention.

G. Emulsification of Silk Protein Aqueous Gel

The emulsification method was the same as for the silk protein aqueous solution in E. described above.

When the silk protein concentration of the gel increases above approximately 6%, the gel and oily component mix, making it difficult to achieve emulsification by stirring alone.

With an increasing concentration, emulsification is facilitated by the addition of water during the stirring.

Water must be added in an amount of about double the equivalent of the silk protein.

That is, the stirring may be carried out with the addition of 10-20 g of water to 100 g of gel at a 10% concentration.

Emulsification after gelling the silk protein aqueous solution requires more gelling steps than emulsification with the silk protein aqueous solution, and is therefore industrially undesirable.

However, emulsification with the silk protein aqueous gel has the advantage of allowing the emulsification to be accomplished even with a lower proportion of the oily component than with a silk protein aqueous solution.

That is, since using an aqueous gel alters the proportion of the oil component and silk fibroin within a wide range from that of the silk protein aqueous solution, even with the same content, an advantage is provided in that it becomes possible to obtain an emulsion with a different property.

The reason is believed to be that as a result of the loose bonds between molecules in the silk fibroin which are formed by gelling of the silk protein aqueous solution, not all of the silk fibroin chains have to bond with the oily component.

As necessary, there may be appropriately added to the emulsified cosmetic material of the invention components commonly used in cosmetic materials, such as pH regulators, preservatives, thickeners, humectants, antibacterial agents, anti-inflammatory agents, pigments, aromatics, antioxidants, ultraviolet absorbers, vitamins, organic or inorganic powders, alcohols, sugars and the like, so long as the function and effect of the invention are not impaired.

EXAMPLE 1

Emulsification of Oily Component by Silk Protein Aqueous Solution

Cocoon shells from domesticated silkworm cocoons produced in the spring of 2001 were dried, boiled and reeled to obtain raw silk for use as a raw material, and 300 g of the raw silk was boiled for 50 minutes in 12 l of water with 6 g of sodium carbonate to accomplish scouring.

The scouring reduction was 25.7%, and it was assumed that the obtained silk yarn contained at least 99% fibroin.

The silk yarn (150 g) was dissolved with a solution containing calcium chloride, ethanol and water in a molar ratio of 1:2:8 (in a 10-fold amount with respect to the silk yarn).

The dissolution was carried out at 75-80° C. for 60 minutes and followed by dialysis.

The dialysis was carried out by placing the dissolved solution in a dialysis membrane (UC36-32-100, Sanko Junyaku Co., Ltd.) and immersing the membrane in purified water.

No fibroin H chains were found in the fibroin electrophoresis image after dialysis, but a few L chains were found, and the weight-average molecular weight by chromatography was approximately 240,000.

The concentration of the silk protein aqueous solution after dialysis was 8.2%.

The concentration was diluted with purified water to prepare silk protein aqueous solutions at 4.0%, 2.0%, 1.0% and 0.2% in addition to the 8.2% solution.

The 8.2% silk aqueous solution was dried in a chamber at 5° C. while still in the dialysis membrane, to obtain a silk aqueous solution with a concentration of 13.2%.

Olive oil was added to the silk protein aqueous solutions having these different concentrations, and stirring (coffee mixer, approximately 20 seconds) was carried out for emulsification.

A 0.1-0.3 g portion of each stirred emulsion was placed on a forearm and thoroughly spread over an area of about 100 cm² with a finger for coating.

The range of usability of each emulsion as a cosmetic for application onto the skin was evaluated based on the ease of spreading (spreadability) of the emulsions and production of small masses from the emulsion (crumbling feel).

Figure 1:
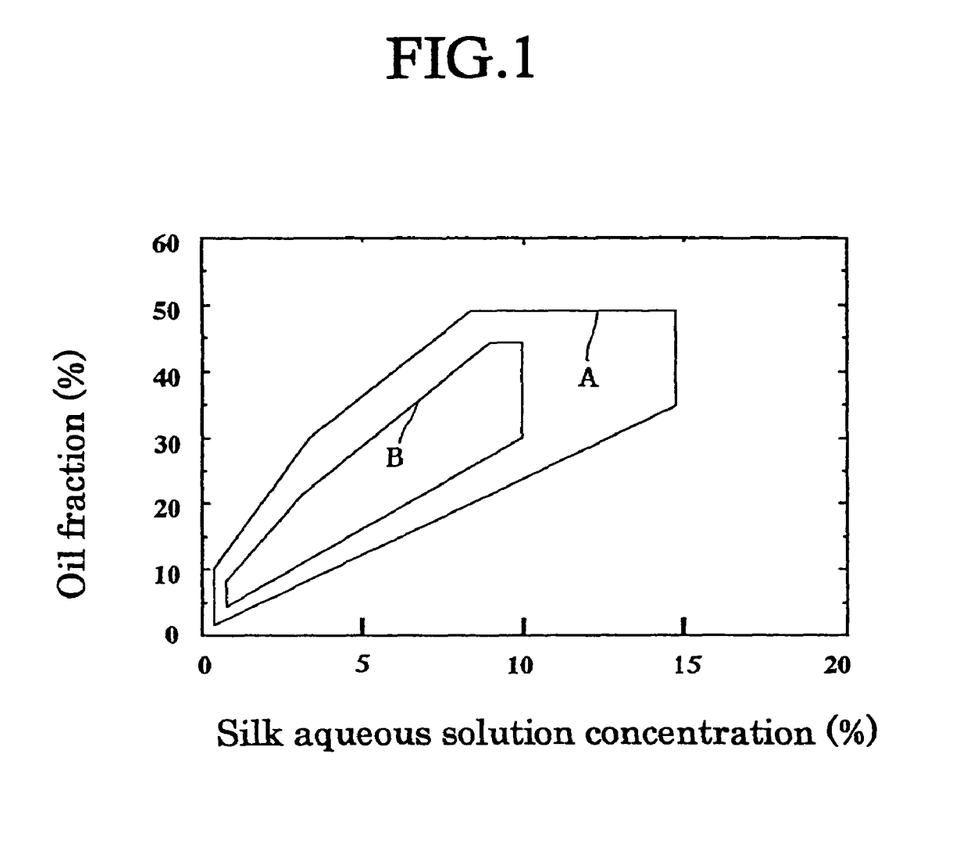
FIG. 1 is a graph showing the relationship between oily component and silk aqueous solution concentration for a silk cream.

The results are shown in FIG. 1.

The horizontal axis in FIG. 1 indicates silk protein aqueous solution protein concentration (%).

The vertical axis indicates the oil fraction =100×oily component (g)/(silk protein aqueous solution (g)+oily component (g)).

The range of use as latex or creams is the region defined by line A, and preferably the region defined by line B.

EXAMPLE 2

Emulsion from Silk Protein Aqueous Solution Prepared from Dried Amorphous Silk Protein (Film or Powder)

The 4.0% concentration silk protein aqueous solution prepared in Example 1 was cast onto a plastic sheet in a chamber at 25° C., 40% RH and dried with air blowing to fabricate a silk film.

The obtained amorphous silk film was immersed in water at 20° C. and dissolved to prepare silk protein aqueous solutions with concentrations of 6.0%, 4.0%, 2.0% and 1.0%.

In the same manner as Example 1, olive oil was added to these solutions and mixing was carried out for emulsification.

Evaluation of the relationship between the silk protein aqueous solution concentration and oil fraction of each emulsion suitable for use as a cosmetic material provided the same results shown in FIG. 1.

EXAMPLE 3

Emulsification of Oily Component with Silk Protein Aqueous Gel

A 300 g portion of domesticated silkworm cocoon shell was immersed in a boiling solution containing 6 g of sodium carbonate and 12 liters of water and then scoured for 60 minutes.

A 195 g portion of this silk yarn was dissolved in a solution containing 392 g of calcium chloride, 508 g of water and 325 g of ethanol.

The temperature of the solution was 75-85° C., and the dissolution time was 3 hours.

Dialysis was performed with tap water for the first two days, followed by two days with purified water, replaced 8 times.

No fibroin H chains or L chains were found in the electrophoresis image for the silk aqueous solution, and the average molecular weight was approximately 65,000 based on gel chromatography.

The concentration of the silk aqueous solution was 14.1%.

Solutions with concentrations of 6.0%, 3.0%, 1.0% and 0.2% were also prepared, and these were allowed to stand at 70° C. for gelling.

Olive oil was added to the obtained silk protein aqueous gels, and stirring was carried out (coffee mixer, approximately 30 seconds) for emulsification.

A 0.1-0.3 g amount of each of the obtained emulsions was placed on a forearm and thoroughly spread over an area of about 100 cm² with a finger (at a rate of about 20-200 cm/sec and a load of about 20-200 g)to coat the skin. The range of usability of each emulsion as a cosmetic was evaluated based on the ease of spreading and production of small masses from the emulsion (crumbling feel).

Figure 2:
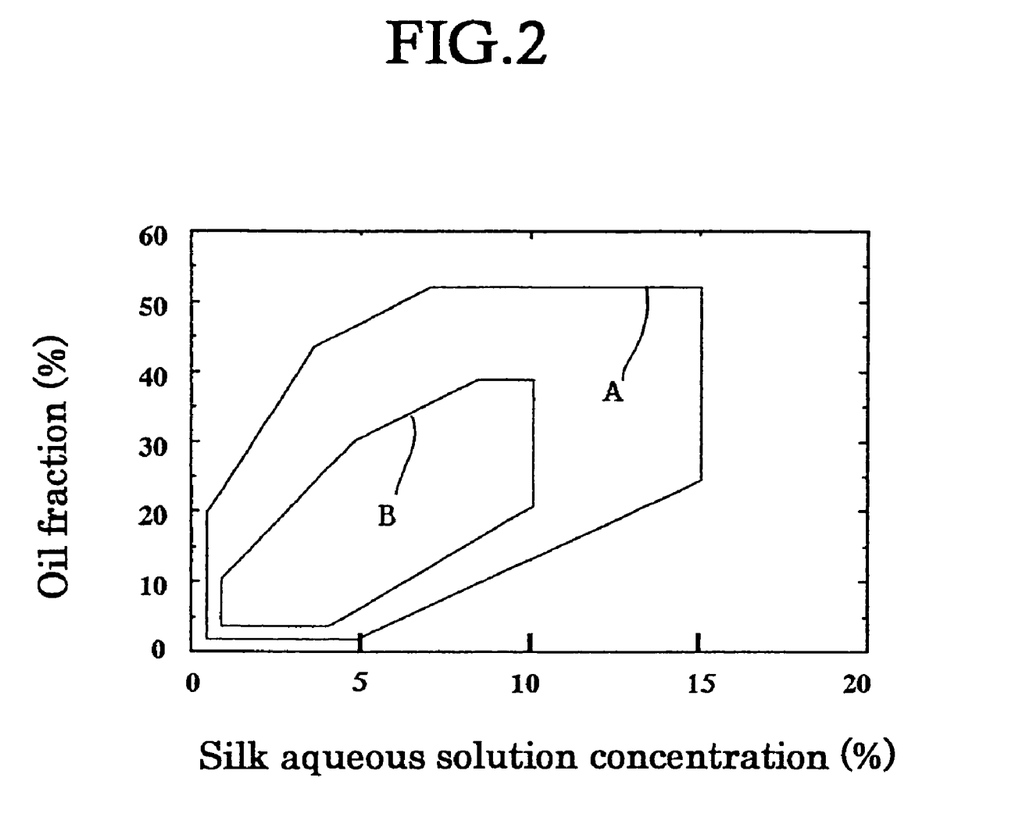
FIG. 2 is a graph showing the relationship between oily component and silk gel concentration for a silk cream.

The results are shown in FIG. 2.

The horizontal axis in FIG. 2 indicates silk protein aqueous solution protein concentration (%).

The vertical axis indicates the oil fraction=100×oily component (g)/(silk protein aqueous solution (g)+oily component (g)+W(g)).

W is the weight of water added during the stirring, in the case of a high gel density.

The range of use as latex or creams is the region defined by line A, and preferably the region defined by line B.

EXAMPLE 4

Preparation of Silk Protein Aqueous Gels:

A 300 g portion of domesticated silkworm cocoon shell was immersed in a boiling solution (approximately 100° C.) containing 6 g of sodium carbonate and 12 liters of water, and then scoured for 60 minutes.

A 150 g portion of this silk yarn was dissolved in a solution containing 392 g of calcium chloride, 508 g of water and 325 g of ethanol.

The temperature of the solution was 75-85° C., and the dissolution time was 2 hours.

Dialysis was performed with tap water for the first two days, followed by two days with purified water and replaced 8 times.

No fibroin H chains or L chains were found in the electrophoresis image for the silk protein aqueous solution, and the average molecular weight was approximately 130,000 based on gel chromatography.

The obtained silk protein aqueous solution with a 9.41% concentration was diluted with water to prepare additional silk protein aqueous solutions with concentrations of 3.12% and 0.20%.

The silk protein aqueous solutions were placed in beakers and allowed to stand in a thermostatic chamber to evaluate the gelling time.

An autoclave was used for the temperature of 120° C.

Gelling is confirmed by translucency of the silk protein aqueous solution, but it is defined as a state in which the silk protein aqueous solution does not pour from a beaker when the beaker is overturned.

However, when the silk protein aqueous solution concentration is less than about 3%, the gel state becomes very fragile and pours out by merely overturning the beaker, and therefore air bubbles in the gel are noted and the gelling point is defined as the point at which air bubbles do not move, even when the gel is inclined at 10-30° from the horizontal.

Figure 3:
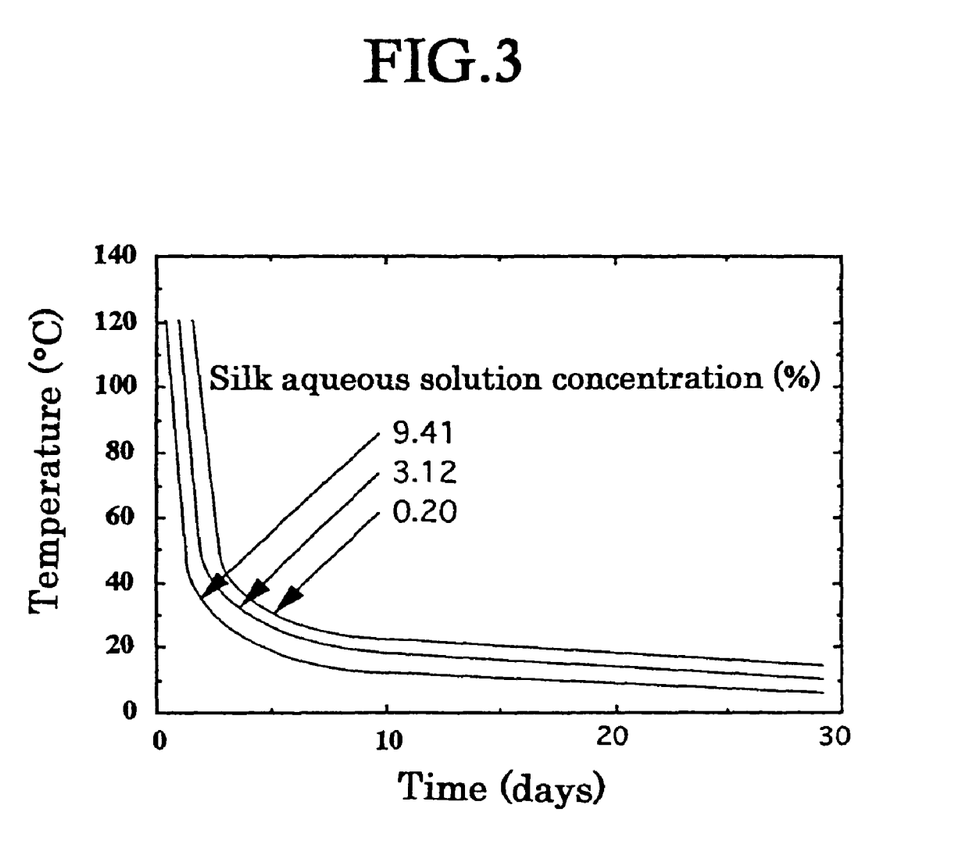
FIG. 3 is a graph showing the relationship between concentration (%), temperature (° C.) and time (days) for gelled silk aqueous solutions.
Figure 4:
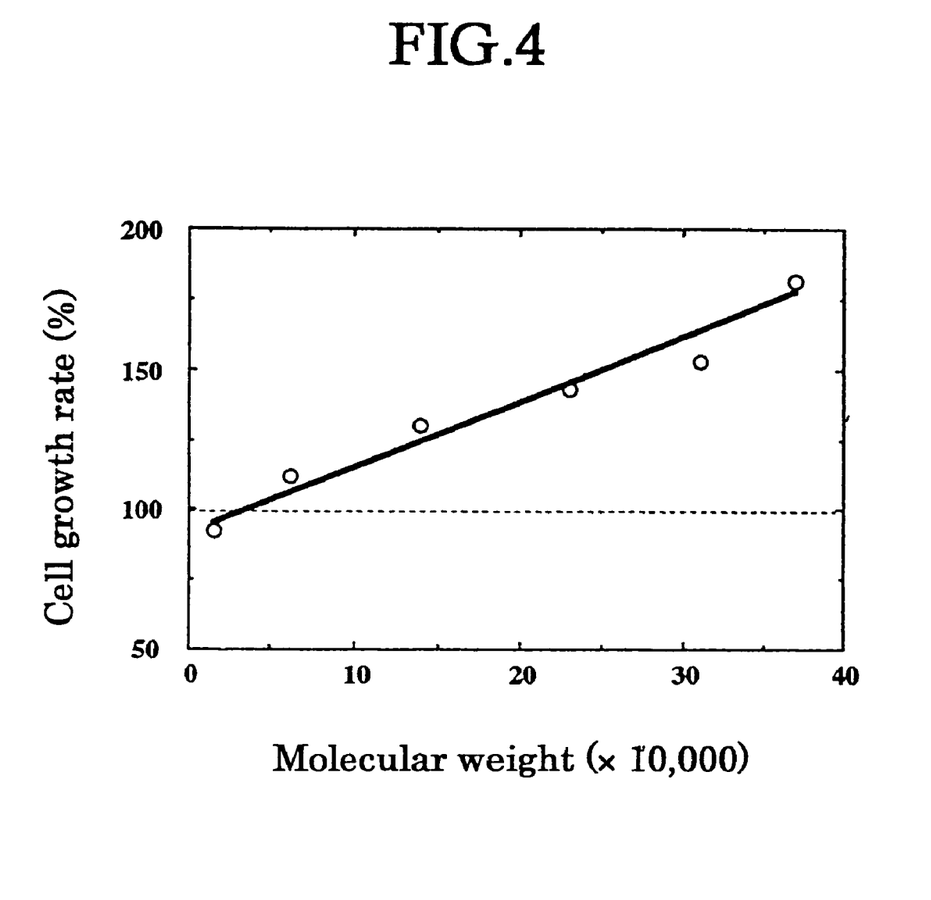
FIG. 4 is a graph showing the relationship between silk protein (weight) average molecular weight and cell growth rate (%).

The results are shown in FIG. 3.

The silk protein aqueous solution gels in about 2-4 days at a temperature of 50-80° C.

The gelling time will differ depending on the heat and the shear force produced by stirring, etc.

COMPARATIVE EXAMPLE

Emulsification of Oily Component by Sericin Aqueous Solution

After separating domesticated silkworm cocoon shells (5.0 g) into several sheets, they were immersed for 15 minutes in a 40-fold amount (200 g) of 8 M urea water at 80° C. and thoroughly agitated.

The reduction achieved by scouring was 21.2%.

The scouring solution was dialyzed (4 times every two hours) with a 50-fold amount of water.

The solution had a concentration of 0.25% after completion of the dialysis, and had already gelled.

The gelled sericin converts to a sericin aqueous solution when the temperature is increased.

The solution was boiled for different boiling times.

Such aqueous solutions were obtained with sericin concentrations of 1.85%, 3.24% and 5.48%.

The aqueous solutions at concentrations of 3.24% and 5.48% contained floating precipitates during the boiling.

Olive oil was added to each of the sericin aqueous solutions prior to stirring.

The emulsified emulsions obtained by stirring were spread onto a hand, and the touch and spreadability as cosmetic products were evaluated.

As a result, although emulsions were obtained with concentrations in a range of less than 6%, they tended to be softer at higher temperatures and harder at lower temperatures during use, as compared to using a silk protein aqueous solution composed mainly of fibroin.

The sericin aqueous solution may be used as an emulsifier with a concentration in a range of 0.1-6%, but it is preferably from several tenths of a percent to 4%, and more preferably from 0.1% to 2%.

With increasing proportion of fibroin mixed with the sericin aqueous solution, the concentration may be increased.

EXPERIMENT EXAMPLES

Experiment Example 1

Skin Irritation

An emulsified cream according to the invention and two commercial cosmetic creams by different companies not containing silk protein aqueous solutions were subjected to a patch test for skin irritation.

As the emulsified cream of the invention there was used a silk cream obtained by using a silk protein aqueous gel (silk gel) with a silk protein concentration of 4.5% obtained by the method of Example 4 in stirred admixture with the cosmetic materials shown in Table 1 in the listed proportions.

These three samples were subjected to a patch test by 10 women (one teenaged woman, 4 women in their 20s, 3 women in their 30s and 2 women in their 40s, all with allergies).

The Finn-Chamber patch test was employed, whereby the silk cream and the creams by companies A and B were applied to the inside area of the forearm and the skin reaction was judged based on a judgment standard after 48 hours and after 72 hours (Nakagawa, Shojiro: Contact Dermatitis Care and Clinical Immunity).

The degree of irritation at the site of application was visually examined 48 hours and 72 hours after application and judged and scored as shown in Table 2. The total score for each sample was divided by the number of testers and multiplied by 100 to give the irritation indexes shown in Table 3.

Table 3 shows that the silk cream exhibited no skin irritation while the other company creams containing no silk protein exhibited skin irritation.

Experiment Example 2

Cell Growth Promotion by Silk Protein Composed Mainly of Amorphous Silk Fibroin

A 5.0 g portion of domesticated silkworm cocoon shells was immersed in 200 ml of 8 M urea water at 80° C. and then stirred and scoured.

The scouring times were (1) 20 minutes and (2) 10 minutes, and the scouring reductions were (1) 25.8% and (2) 21.2%, respectively.

Also, 5.0 g of cocoon shells was boiled and scoured with 200 ml of water for (3) 30 minutes and (4) 15 minutes.

The scouring reductions were (3) 16.0% and (4) 8.7%, respectively.

An unscoured cocoon shell was prepared as (5).

Sample (1) had virtually all of the sericin removed, with at least 99% believed to be fibroin.

In order to obtain the sericin content values for the silk protein samples (1) to (5), they were immersed for 90 minutes in a boiling solution of 0.05 g of sodium carbonate in 100 ml of water, and then thoroughly stirred and scoured.

The weight reduction after scouring was calculated in terms of sericin.

Also, sericin silkworm cocoon shells (100% sericin, as sample (8)) were added to domesticated silkworm filament cocoon shells to prepare samples with sericin contents of 50.0% (6) and 75.0% (7).

Coating of the silk onto cell culturing vessels was accomplished in the following manner.

A 0.01 g portion of each of the silk protein samples (1) to (8) was dissolved in 1.0 ml of 9 M LiSCN and each solution was dialyzed 5 times with a 50-fold amount of water, and then 1 ml of a 0.0025% solution of each dialyzed silk protein was placed in a cell culturing Petri dish (35 mm$\phi$, Falcon), subjected to air blowing, washed 3 times with 2 ml of PBS, air dried again and sterilized with 70% ethanol.

The cells used were human skin fibroblasts purchased from Kurabo Co., Ltd.

The medium used was skin fibroblast growth low serum medium also purchased from Kurabo Co., Ltd.

The culturing was carried out for 3 days after placing 2 ml of medium and seeding 70,000 cells in each Petri dish coated with silk protein.

The number of cells was measured by placing 0.1 ml of Arama Blue (Iwaki Co.) in each Petri dish, heating at 37° C. for 2 hours and then determining the number of viable cells based on the amount of pigment reduction calculated from the absorbance at 570 nm and 600 nm.

A Petri dish not coated with silk protein was used as a control (100%), and the numbers for the cell growth on the silk protein-coated Petri dishes are shown in Table 4.

The silk protein-coated dishes all showed superior cell growth with respect to the control group independently of the sericin content.

Experiment Example 3

Fibroin Molecular Weight and Cell Growth Promotion

After placing 0.5 g of sodium carbonate in 1,000 cc of water, the solution was boiled (100° C.) and 10.0 g of domesticated silkworm cocoon shells was immersed therein during the boiling and stirred for scouring.

The scouring times were (1) 5 minutes, (2) 20 minutes, (3) 60 minutes, (4) 130 minutes and (5) 180 minutes.

The scouring reductions were (1) 22.3%, (2) 24.5%, (3) 25.1%, (4) 25.5% and (5) 26.2%.

Samples (4) and (5) were believed to contain at least 99% fibroin.

The relationship between (weight-average) molecular weight and cell growth property was examined for each of the silk proteins.

The average molecular weight measurement was accomplished using a gel chromatography column, with elution of the sample using 8 M urea/40 mMTris-$H_2SO_4$ (pH 8) (0.6 ml/min) and monitoring at 275 nm.

The molecular weight measuring column used was a Superdex 200 Prep grade (Pharmacia).

The cell growth properties of samples (1) to (5) were measured in the manner described below.

First, the silk was coated onto cell culturing vessels in the following manner.

A 0.01 g portion of each of the silk proteins of (1) to (5) was dissolved in 1 ml of 9 M LiSCN, and each solution was dialyzed 4 times with a 50-fold amount of water to prepare silk protein aqueous solutions.

A 1 ml portion of a 0.0025% solution of each of these silk proteins was placed in a cell culturing Petri dish (35 mm., Falcon), subjected to air blowing, washed 3 times with 2 ml of PBS, air dried again and sterilized with 70% ethanol.

The cells used were human skin fibroblasts purchased from Kurabo Co., Ltd., and the medium used was skin fibroblast growth low serum medium also purchased from Kurabo Co., Ltd.

The culturing was carried out for 3 days after placing 2 ml of medium and seeding 70,000 cells in each Petri dish coated with silk protein.

The number of cells was measured by placing 0.1 ml of Arama Blue (Iwaki Co.) in each Petri dish, heating at 37° C. for 2 hours and then determining the number of viable cells based on the amount of pigment reduction calculated from the absorbance at 570 nm and 600 nm.

A Petri dish not coated with silk protein was used as a control (100%), and the numbers for the cell growth on the silk protein coated Petri dishes are shown in Table 4.

Although the cell growth property diminished with a lower fibroin molecular weight, a cell growth promoting property was exhibited with a fibroin molecular weight of about 20,000 and greater.

The present invention as explained above is not limited to the aforementioned examples and may incorporate various modifications so long as the function and effect described in the present specification are still achieved.

For example, the invention may be utilized in such fields as foods (chocolate emulsifiers and the like), medical products (ointments, etc.), cleaning products (detergents, etc.) and the like.

INDUSTRIAL APPLICABILITY

The present invention relates to a protein-based emulsifier and to a method of producing emulsified cosmetic materials using the emulsifier, but insofar as it is within the scope of its principle, it may be applied to any type of cosmetic use, and in any field in which the same effect may be expected, such as in the field of foods, medical products, cleaning products or the like.

TABLE 1

Silk cream mixing proportions

| | |
|---|---|
| Silk gel | 81.0 (g) |
| Olive oil (squalane) | 7.5 |
| Jojoba oil | 7.5 |
| Glycerin | 2.8 |
| Tocopherol | 0.5 |
| Glycyrrhiza ($K_2$) | 0.5 |
| Paraben | 0.2 |

TABLE 2

Patch test irritation judgment and scores

| Irritation judgment | Score |
|---|---|
| No reaction: (−) | 0 |
| Slight reddening: (±) | 0.5 |
| Definite reddening: (+) | 1.0 |
| Reddening with edema or: (++) infiltration | 2.0 |

TABLE 3

Patch test irritation index

| | After 48 hours | After 72 hours |
|---|---|---|
| A Co. cream | 10 | 20 |
| B Co. cream | 10 | 15 |
| Silk cream | 0 | 0 |

TABLE 4

Sericin contents and cell growth properties

| Silk protein | Sericin content (%) | Cell growth rate (%) |
|---|---|---|
| Control group | | 100 |
| (1) | 0.0 | 269 |
| (2) | 5.4 | 270 |
| (3) | 11.7 | 252 |
| (4) | 19.3 | 265 |
| (5) | 26.5 | 218 |
| (6) | 50.0 | 233 |
| (7) | 75.0 | 244 |
| (8) | 100.0 | 256 |

The invention claimed is:

1. A method for producing an emulsified cosmetic material having a skin cell growth-promoting property, comprising the steps of: dissolving unscoured, partially scoured or scoured spun silkworm fibers with a neutral salt in the absence of a surfactant to obtain a solution of the silkworm fibers; dialyzing the solution of silkworm fibers with water and removing substances having a molecular weight of 5,000 or lower to form an aqueous solution of silk protein mainly composed of silk fibroin having a degree of crystallization of less than 10% and an average molecular weight of between 40,000 and 370,000; drying the aqueous solution of silk protein to produce an amorphous silk substance; dissolving the amorphous silk substance in water in the absence of a surfactant to regenerate the aqueous solution of silk protein having a concentration of 0.1 to 15% and sericin proportion of 50% or lower and emulsifying an oily component with the regenerated aqueous solution of silk protein to produce the emulsified cosmetic material.

2. A method for producing an emulsified cosmetic material having a skin cell growth-promoting property, comprising the steps of: dissolving unscoured, partially scoured or scoured spun silkworm fibers with a neutral salt in the absence of a surfactant to obtain a solution of the silkworm fibers; dialyzing the solution of silkworm fibers with water and removing substances having a molecular of 5,000 or lower to form an aqueous solution of silk protein mainly composed of silk fibroin having a degree of crystallization of less than 10% and an average molecular weight of between 40,000 and 370,000, allowing the aqueous solution of silk protein having a concentration of 0.1 to 15% and sericin proportion of 50% or lower to stand at 40-130° C. to obtain an aqueous gel and emulsifying an oily component with the aqueous gel to produce the emulsifiable cosmetic material.

3. The method of claim 2, additionally comprising the steps of separating the aqueous gel into a supernatant and a precipitate by a centrifugal separator at 8,000 rpm for 10 minutes so that the silk protein concentration of the supernatant is 0.1-2.0, adding water to the precipitate in the same amount as the separated supernatant to form a second aqueous gel; separating the second aqueous gel into a second supernatant and a second precipitate by the centrifugal separator at 8,000 rpm for 10 minutes so that the silk protein concentration of the second supernatant is 0.1-2.0 to form a second aqueous gel and using the second aqueous gel as the aqueous gel to emulsify the oil component.

4. In a method of producing an emulsified cosmetic, the improvement comprising emulsifying an oily component with the emulsified cosmetic material of claim 1.

5. In a method of producing an emulsified cosmetic, the improvement comprising adding water in an amount equal to or double the equivalent of the silk protein in the aqueous gel of claim 2 and then emulsifying the oily component.

6. In a method of producing an emulsified cosmetic, the improvement comprising adding water in an amount equal to or double the equivalent of the silk protein in the aqueous gel of claim 3 and then emulsifying the oily component.

* * * * *